United States Patent
Ahola et al.

(10) Patent No.: US 11,666,552 B2
(45) Date of Patent: Jun. 6, 2023

(54) METHOD FOR MODIFYING RELEASE OF A THERAPEUTICALLY ACTIVE AGENT FROM AN ELASTOMERIC MATRIX

(71) Applicant: Bayer OY, Turku (FI)

(72) Inventors: Manja Ahola, Pikkiö (FI); Risto Hakala, Turku (FI); Piia Hara, Turku (FI); Antti Keinänen, Turku (FI); Henriikka Korolainen, Turku (FI); Jyrki Pihlaja, Paimio (FI)

(73) Assignee: Bayer OY, Turku (FI)

( * ) Notice: Subject to any disclaimer, the term of this patent is extended or adjusted under 35 U.S.C. 154(b) by 65 days.

(21) Appl. No.: 16/649,944

(22) PCT Filed: Sep. 19, 2018

(86) PCT No.: PCT/EP2018/075331
§ 371 (c)(1),
(2) Date: Mar. 23, 2020

(87) PCT Pub. No.: WO2019/063382
PCT Pub. Date: Apr. 4, 2019

(65) Prior Publication Data
US 2020/0276159 A1 Sep. 3, 2020

(30) Foreign Application Priority Data

Sep. 27, 2017 (EP) .................................. 17193367
Apr. 12, 2018 (EP) .................................. 18167014

(51) Int. Cl.
| | |
|---|---|
| A61K 31/405 | (2006.01) |
| A61K 9/50 | (2006.01) |
| A61K 9/48 | (2006.01) |
| A61K 31/196 | (2006.01) |
| A61K 31/5415 | (2006.01) |
| A61K 31/192 | (2006.01) |
| A61K 9/16 | (2006.01) |

(52) U.S. Cl.
CPC .......... *A61K 31/405* (2013.01); *A61K 9/1641* (2013.01); *A61K 9/485* (2013.01); *A61K 9/5026* (2013.01); *A61K 31/192* (2013.01); *A61K 31/196* (2013.01); *A61K 31/5415* (2013.01)

(58) Field of Classification Search
None
See application file for complete search history.

(56) References Cited

U.S. PATENT DOCUMENTS

| | | | | |
|---|---|---|---|---|
| 6,063,395 | A * | 5/2000 | Markkula | ............... A61P 15/00 424/422 |
| 9,434,857 | B2 * | 9/2016 | Ou | ........................ B01J 31/1608 |
| 9,801,831 | B2 * | 10/2017 | Steele | .................. A61K 9/5153 |
| 2002/0136573 | A1 * | 9/2002 | Ogren | ....................... C08J 7/046 399/333 |
| 2007/0043332 | A1 * | 2/2007 | Malcolm | ............... A61K 9/0036 604/500 |
| 2007/0182055 | A1 * | 8/2007 | Eells | ..................... B29C 48/919 264/148 |
| 2009/0142313 | A1 * | 6/2009 | Talling | .................... A61P 15/02 424/93.45 |
| 2018/0008536 | A1 * | 1/2018 | Jukarainen | ........... A61K 31/567 |
| 2019/0358450 | A1 * | 11/2019 | Lo | ........................... A61N 1/36 |

FOREIGN PATENT DOCUMENTS

| | | |
|---|---|---|
| WO | WO0232433 A1 | 4/2002 |
| WO | WO 2011156648 | * 12/2011 |
| WO | WO2013036775 A1 | 3/2013 |
| WO | WO2013110856 A1 | 8/2013 |
| WO | WO2017108676 A1 | 6/2017 |

OTHER PUBLICATIONS

Brinker "Dip Coating" 2013.*
Snorradottir, B.S. et al. (2008). "Release of anti-inflammatory drugs from a silicone elastomer matrix system," Pharmazie, 64: 19-25.
Snorradottir, B.S. et al. (2011). "Experimental design for optimizing drug release from silicone elastomer matrix and investigation of transdermal drug delivery," European Journal of Pharmaceutical Sciences, 42:559-567.

* cited by examiner

*Primary Examiner* — Danah Al-Awadi
(74) *Attorney, Agent, or Firm* — Morrison & Foerster LLP

(57) ABSTRACT

The present invention relates to a method for modifying release of a therapeutically active agent from an elastomeric matrix, comprising providing a core comprising an elastomeric matrix and a therapeutically active agent; dipping the core to a coating solution of an elastomer, wherein the elastomer comprises 20-35 wt-% of a filler, calculated from the total amount of filler and elastomer; curing the dipped core to provide a coated core. In this method the dipping is provided as a continuous process by pulling the core through the coating solution, using a pulling speed suitable for providing a coating thickness of $\delta$-$100\,\mu m$ the filler is selected from silica, titanium dioxide, barium sulphate, carbon and mixtures thereof; the elastomer comprised in the core and the elastomer comprised in the coating solution are independently selected from poly(dimethyl) siloxanes, polyethylene vinyl acetates (EVAs), polyurethanes (PUs), polyhydroxyethyl methacrylates (PHEMAs) and polymethyl methacrylates (PMMAs).

10 Claims, 5 Drawing Sheets

METHOD FOR MODIFYING RELEASE OF A THERAPEUTICALLY ACTIVE AGENT FROM AN ELASTOMERIC MATRIX

CROSS REFERENCE TO RELATED APPLICATIONS

This application is a national stage application under 35 U.S.C. § 371 of International Application No. PCT/EP2018/075331, filed internationally on Sep. 19, 2018, which claims the benefit of European Application Nos. 17193367.4, filed Sep. 27, 2017 and 18167014.2, filed Apr. 12, 2018.

FIELD OF THE DISCLOSURE

The present disclosure relates to modifying release of a therapeutically active agent from an elastomeric matrix, for example from an elastomeric matrix of a reservoir of an intrauterine system.

BACKGROUND OF THE DISCLOSURE

Elastomeric matrices have been used as reservoirs for therapeutically active agents, i.e. drugs for some time. Such reservoirs are used for example in sub-cutaneous implants and intrauterine systems (IUS). The release rate of the therapeutically active agent can be controlled by choosing an appropriate material for the elastomeric matrix, but also by coating a core made of elastomer and comprising the therapeutically active agent. The coating typically also controls the initial release of therapeutically active agent, i.e. it limits the burst effect. The coating material may be made of various elastomers, depending on the therapeutically active agent used as well as the intended use of the reservoir. Typically polydimethylsiloxane (PDMS) and its derivatives are used for the reservoir and/or the coating.

A traditional method of coating a core is to extrude a thin coating layer as a tube and to "pull it" over the core. This could be done by expanding the membrane either with pressurized air or vacuum or by swelling of the membrane in a suitable solvent and removal of the solvent after the drug containing core has been inserter in the membrane tube. Another possible coating method is extrusion coating. These well-known methods are however only suitable for silicone membranes with larger thickness (such as about 150 µm or more) but the methods fail if a very thin membrane (below 100 µm) is needed. Thus, addition of fillers such as silica and membrane thickness are important factors influencing the drug release rate. An insufficient release rate for a thick membrane might be obtained in particular for drugs which are poorly soluble in silicon polymers, such as non-steroidal-anti-inflammatory drugs (NSAID).

Moreover, this type of manufacturing method can be cumbersome and lead to problems. A still further problem is that the coating may not completely adhere to the outer surface of the core, which impacts the drug release and thus may cause trouble during use.

SUMMARY OF THE DISCLOSURE

Thus, there exists a need to provide an alternative method for modifying release of a therapeutically active agent from an elastomeric matrix. Such method would need to be suitable in cases where very thin membranes are needed in a release system.

There exists thus a need to provide a method for applying a thin silicon elastomer membrane on drug containing core, which adheres completely to the core material.

As the drug release is dependent on the physicochemical properties of the drug, such as molecular weight and hydrophobicity, it is a further object of the disclosure to provide a method to modify the drug release of a therapeutically active agent from an elastomeric matrix (core).

In some embodiments, a process for manufacturing of a drug delivery system is provided, which is coated with a silicon based membrane, with a membrane thickness below 100 µm and a product obtained by such method.

In some embodiments, a drug delivery system with a silicon based membrane is provided, with membrane thickness of 10 to 100 µm.

In some embodiments, a drug delivery system containing Indomethacin as therapeutically active agent in the elastomeric matrix (core) coated with an PDMS elastomer membrane is provided, with membrane thickness of 10 to 100 µm.

TERMS AND DEFINITIONS

Figure 1:
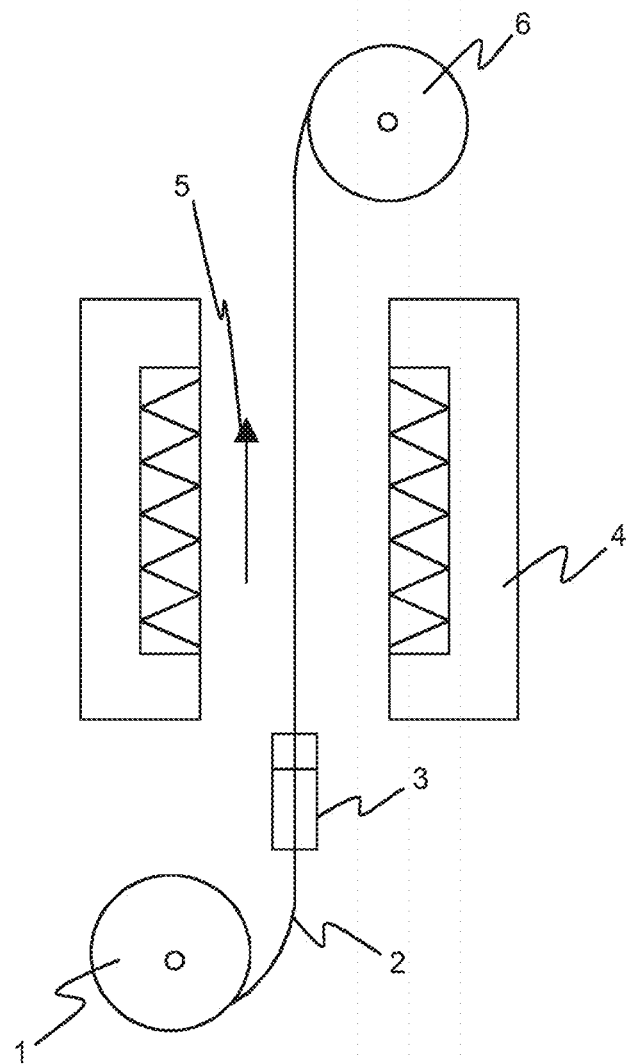
FIG. 1 schematically illustrates a device usable in the present method, according to some embodiments.

In the context of this invention the following terms are used:
PDMS=Polydimethylsiloxane
Elastomer=Silicone with filler
PDMS Elastomer=PDMS with filler
Core: The core contains the therapeutically active agent (drug). Synonymously the term material 2 is used.
Matrix=Carrier Material for the therapeutically active agent→Matrix containing the therapeutically active agent=Core
Coating Solution: The coating solution is a solution of the elastomer (which is a siloxane containing the filler and optionally further additives
Additives: Cross linking agent and catalyst.

DETAILED DESCRIPTION

The present description relates to a method for modifying release of a therapeutically active agent from an elastomeric matrix. The method comprises
    providing a core comprising an elastomeric matrix and a therapeutically active agent;
    dipping the core to a coating solution contains 5-40 wt-% elastomer and 95-60 wt-% solvent
    curing the dipped core to provide a coated core;
Wherein
    the elastomer dissolved in the solvent is comprising 20-35 wt-% of a filler, calculated from the total amount of filler and elastomer; —the dipping is provided as a continuous process by pulling the core through the coating solution, using a pulling speed suitable for providing a coating thickness of 5-100 µm;
    the filler is selected from silica, titanium dioxide, barium sulphate, carbon and mixtures thereof; and
    the elastomer comprised in the core and the elastomer comprised in the coating solution are independently selected from poly(dimethyl) siloxanes, polyethylene vinyl acetates (EVAs), polyurethanes (PUs), polyhydroxyethyl methacrylates (PHEMAs) and polymethyl methacrylates (PMMAs).

The present method thus relates to a dipping method for coating a core comprising an elastomeric matrix and a therapeutically active agent. Dipping is carried out as a continuous process by pulling the core through the coating solution, using a pulling speed suitable for providing a coating thickness of 5-100 µm. A person skilled in the art is readily able to determine a suitable pulling speed, by carrying out a few simple experiments. A typical pulling speed is in the range of 2.5 to 25 mm/s. Particular preferred is a pulling speed of 6-15 mm/s. Some specific combinations of the process conditions are also given below and in the Experimental section. Indeed, the thickness of the achieved coating is influenced not only by the pulling speed (membrane thickness increases with pulling speed), but also by the coating solution (for example its viscosity) and to some extent also by the length the core passes in the coating solution. Also the distance between the container comprising the coating solution and the curing apparatus can have an influence on the thickness of the finished coating, depending on the viscosity of the coating solution.

Once the core has passed in the coating solution, it is subjected to curing. Curing in this respect means polymerisation and/or cross-linking, depending on the elastomer used. Curing can be carried out in one, two, three or more steps, typically in one or two steps. When curing is carried out in more than one step, a first curing step is preferably carried out essentially immediately the core has passed through the coating solution, in order to prevent the coating solution from dripping off the core. The aim of the curing step is then to cure the coating solution to an extent that is sufficient for fixing the coating on the core so that it can be further handled and moved for example to a separate device for a post-curing.

In some embodiments, the curing is carried out using light, and/or heat, i.e. the curing is induced by infrared radiation, ultraviolet radiation, heat or any combination thereof. The dimensions and location of the curing part of the device are selected according to the number of curing steps to be used as well as the other characteristics of the device, for example whether it is for continuous processing or for batch processing. An example of a device is schematically illustrated in the enclosed FIG. 1 and explained in more detail below.

If the elastomer is liquid enough the dipping process can be operated without solvent. However, preferably a solvent is used, whereby the concentration of the elastomer in the solvent is in the range of 5-40 wt-% elastomer (60-95 wt-% solvent). The elastomer comprises a filler selected from silica, titanium dioxide ($TiO_2$), barium sulphate ($BaSO_4$), carbon and mixtures thereof. Some of these fillers are also known as colorants.

The elastomer, which is a mixture of filler and silicone, comprises 20-35 wt-% of filler and 65-80 wt-% of silicone. In other words, the amount of filler is such that the cured coating comprises 20-35 wt-% filler.

In some embodiments, also a solvent is used in the coating solution. In this case, the amount of solvent in the coating solution can be 60-95 wt-% and the solvent is selected from non-polar solvents. The solvent can be for example xylene, t-butyl acetate, ethyl acetate, butyl acetate, hexane, cyclohexane, toluene, acetonitrile, benzene, chloroform, dichloromethane or mixtures thereof. Preferred is xylene. Further, in this case, the coating solution comprises 60-95 wt-% of solvent and 5-40 wt-% of a mixture of elastomer and optionally further additives (cross-linking agent and catalyst).

Preferred is a coating solution containing 85-90 wt-% solvent.

Furthermore, in some embodiments, the amount of elastomer in the coating solution is 1-25 wt-%. The amount of elastomer in the coating solution can vary for example from 1, 2, 5, 7, 9, 10, 14, 15, 19, 20 or 22 wt-% up to 2, 5, 7, 9, 10, 14, 15, 19, 20, 22 or 25 wt-%.

The elastomer comprised in the core and the elastomer comprised in the coating solution are independently selected from poly(dimethyl) siloxanes (PDMSs), polyethylene vinyl acetates (EVAs), polyurethanes (PUs), polyhydroxyethyl methacrylates (PHEMAs) and polymethyl methacrylates (PMMAs), wherein PDMS is preferred. The elastomer is thus such that it can be dissolved in the solvents mentioned above and it can preferably remain in a dissolved state for a significant period of time (typically about 1 to 2 hours), thus removing the necessity to having to mix the coating solution during coating.

The therapeutically active agent can be selected from indomethacine, diclofenac, piroxicam, meloxicam and ketoprofen. Preferred therapeutically active agent is indomethacin (IND).

Manufacturing of the therapeutically active agent (drug) containing core is according to standard methods known in the art, e.g. by mixing the drug powder with the (silicon) elastomer with a blade mixer and extruding the mixture to form a hollow rod.

In some embodiments, the elastomer comprised in the core is the same as the elastomer comprised in the coating solution. In some embodiments, the elastomer in both the core and the coating is polydimethylsiloxane (PDMS).

In some embodiments, the pulling speed is 1-30 mm/s. Preferred pulling speed is 5 to 20 mm/s. The time of exposure of the core to the curing media (irradiation and/or heat), i.e. the curing time, can then be easily calculated (when knowing the size of the curing device), and can be for example 10-60 s. For example, for a height of the curing device of one meter, the residence time can be for example 25-30 s, depending on the heating power capacity of the curing device (in the context of this application likewise the terms curing oven or curing tunnel are used). Indeed, increasing curing power (for example heat) can shorten the time required for curing, but it may also have an effect on impurities formed in the core during curing.

As mentioned above, the pulling speed influences the thickness of the coating, but is not the only factor influencing it. The time of exposure of the core to the coating solution is dependent on distance the core travels in the coating solution, i.e. on the size of the bath of coating solution. In one example, the residence time in the bath or container of coating solution can be about 7-15 seconds.

When a thick layer of coating is required, this can be achieved in three different ways. Either the coating solution can be made more viscous, for example by reducing the amount of solvent.

Another option to modify the thickness of the coating is by varying the pulling speed. With higher pulling speed thicker membranes are achieved as the coating solution reaches the curing (oven) tunnel faster, thus less coating solution has drained from the core, when reaching the curing tunnel.

The third option is to apply two or more layers of coating, i.e. passing the core through the coating device a second, third, fourth etc. time. Preferably, between each application of the coating solution, the previous layer is fully cured. It is also, in some cases, possible to apply a second layer of coating only after a pre-curing step.

FIG. 1 schematically illustrates a device usable in the present method. The device comprises a first coil 1 of the material 2 (in the context of this application likewise the terms tube or core are used) to be coated, located at the bottom of the device. This material contains also the therapeutically active agent. The material 2 is then directed to a container 3 comprising the coating solution. Thereafter, the material 2 is directed to a curing part 4 (curing tunnel), which in this embodiment consists of two infrared irradiators arranged facing one another such that the material 2 can pass through the curing part 4 in the direction indicated by an arrow 5. After curing in the curing part 4, the material 2 (now coated) is arranged on a second coil 6.

The same device (as shown in FIG. 1) can be used for both (a) batch mode and (b) continuous mode production. In both modes material 2 (core) is pulled through the container 3 which comprises the coating solution.

However, in batch mode the coated core is stopped, when inside the curing part 4 (curing tunnel) by pausing the second coil 6. In other words during the curing of the coated core movement 5 is discontinued.

Contrary to this, in continuous mode not only the coating but also the curing is continuous. Thus in continuous mode a longer curing tunnel (oven) is required to apply the same radiation on the coated core as in batch mode.

FIGS. 2-5 will be discussed in more detail below in the Examples.

EXAMPLES

Materials Used

A poly(dimethyl) siloxanes core of a sample (continuous tube) to be coated according to the present description comprised indomethacin as active agent (from Esteve Quimica) and R972 (pharma) silica (from Evonik). The core was hollow, having an inner diameter of 1.0 mm and an outer diameter of 2.4 mm.

The coating material comprised PDMS (polydimethylsiloxane) diluted in xylene (pre-prepared 85 wt-% xylene solution from Trelyst). The three different concentrations, namely 85, 90 and 95 wt-% have been used. The 90 and 95 wt-% solution has been prepared by adding further xylene (from Merck) to the 85 wt-% xylene solution. Additionally, the PDMS comprises silica as filler, also in three different concentrations, namely 22, 27 and 32 wt-%. The coating solutions were prepared by mixing the ingredients using a magnetic stirrer.

1. Coating Process
1.1 Coating Process in Batch Mode

The coating was carried out using a device according to FIG. 1. The pulling speed through the container 3 with the coating solution was set and the pre-curing oven heated to a temperature of 135° C. gradually (60, 100, 120 and 135° C.). Two different pulling speeds were used for the coating, namely 2.5 mm/s and 25 mm/s.

The continuous tube was attached to the device by one of its ends. As the device functioned in a batch-mode, the therapeutically active agent containing, continuous poly (dimethyl) siloxane tube (core) was pulled through the coating solution for a length corresponding to the length of the curing oven, i.e. pulling was interrupted when a full length of the continuous tube was inside the curing oven. In the present case, the length of each cured part of the continuous tube was 15 cm. Thereafter, the continuous tube was left in the oven for about 10 minutes.

The portion of the continuous tube that was cured, was cut from the rest of the continuous tube and the cut parts were transferred to a drying rack. Thereafter the drying rack was transferred to another oven for final curing. The post-curing time was 90 min and the temperature was 80° C.

After final curing, the tubes were removed from the oven and approximately 3 cm from each end was cut out and disregarded. Thereafter a thin sample was cut from each end for measuring the thickness of the coating with a microscope.

1.2 Coating Process in Continuous Mode

The coating was carried out using a device according to FIG. 1, using infrared irradiation. The pulling speed (through container 3 and curing tunnel 4) was set and the curing oven set to a power of 30%. Several different pulling speeds were used for the coating, namely 7 mm/s, 12 mm/s and 15 mm/s.

The therapeutically drug containing continuous poly(dimethyl) siloxane tube (core) was attached to the device by one of its ends and pulled through the coating solution. The length of the curing oven was 1.0 m. The post-curing time was 60 min and the temperature was 105° C. Thereafter a thin sample was cut from each end for measuring the thickness of the coating with a microscope.

Further samples were prepared to study the effect of the number of coating layers, i.e. the number of dippings. These samples are named groups A, B and C. The dip coating solution was as listed above (from Trelyst), the amount of elastomer (PDMS and filler) was varied by adding xylene (from Merck) if necessary.

When a second or further coating layer was applied, the once (twice etc.) cured piece of continuous tube was subjected to a second (or further) coating step after final curing, as described above, i.e. each coating layer was cured before application of a further layer. The coating layers were attached to one another. Three groups have been prepared to investigate membrane thickness and drug release in dependency of the number of coating steps.

Group A consisted of samples coated with a pre-prepared solution (from Trelyst) comprising 15 wt-% of PDMS elastomer containing 27 wt-% of silica as filler, in xylene. Dipping was carried out once. The total thickness of the coating was 0.075 mm.

Group B consisted of samples coated with the a.m. solution from Trelyst wherein the concentration of PDMS elastomer has been lowered to 10 wt-% by adding xylene. Dipping was carried out twice. The total thickness of the coating was 0.05 mm.

Group C consisted of samples coated with the same solution as used for group B but dipping was carried out three times. The total thickness of the coating was 0.075 mm.

2. IUS Sample Preparation
2.2 IUS Sample Preparation, Batch Mode

Pieces having a length of 6 mm were cut from the coated tube (core). Weight, length as well as inner and outer diameters of each piece was measured.

Thereafter each piece of coated tube was positioned on a T-frame of an IUS. If required, the pieces were held in cyclohexane to swell them prior to positioning on the T-frame. If cyclohexane was used, the assembled IUS sample was allowed to rest for at least 2 hours, in order for the cyclohexane to evaporate. The length of each piece as well as the inner and outer diameter of each piece was measured at two different positions after assembly. Likewise, the thickness of the coating was measured at two different positions after assembly.

Tables 1 and 2 below illustrate the average values of some samples (samples 1-20), the average having been calculated on the basis of three parallel samples. XYL stands for xylene and TBA stands for t-butyl acetate.

Table 1 gives the parameters for the coating solution (solvent, amount of solvent and silica content) as well as the pulling speed used. Weight of the coated core as well as the thickness of the coating are also given.

Table 2 gives the measurement results for the dimensions of the coated core before and after assembly on the T-frame, OD standing for outer diameter and ID for inner diameter.

TABLE 1

| Sample | Solvent | Amount of solvent (wt-%) | Silica content[1] (wt-%) | Pulling speed (mm/s) | Weight of coated core (mg) | Coating thickness (mm) |
|---|---|---|---|---|---|---|
| 1 | XYL | 90 | 27 | 2.5 | 27.42 | 0.03 |
| 2 | XYL | 90 | 27 | 25 | 22.01 | 0.02 |
| 3 | XYL | 95 | 32 | 2.5 | 29.30 | <0.01 |
| 4 | XYL | 95 | 32 | 25 | 29.25 | <0.01 |
| 5 | XYL | 95 | 22 | 2.5 | 29.18 | <0.01 |
| 6 | XYL | 95 | 22 | 25 | 29.43 | <0.01 |
| 7 | XYL | 85 | 32 | 2.5 | 30.55 | 0.03 |
| 8 | XYL | 85 | 32 | 25 | 32.85 | 0.06 |
| 9 | XYL | 85 | 22 | 2.5 | 31.65 | 0.04 |
| 10 | XYL | 85 | 22 | 25 | 31.41 | 0.06 |
| 11 | TBA | 90 | 27 | 2.5 | 27.71 | <0.01 |
| 12 | TBA | 90 | 27 | 25 | 27.79 | <0.01 |
| 13 | TBA | 95 | 32 | 2.5 | 25.49 | <0.01 |
| 14 | TBA | 95 | 32 | 25 | 25.33 | <0.01 |
| 15 | TBA | 95 | 22 | 2.5 | 26.10 | <0.01 |
| 16 | TBA | 95 | 22 | 25 | 27.39 | <0.01 |
| 17 | TBA | 85 | 32 | 2.5 | 29.53 | 0.04 |
| 18 | TBA | 85 | 32 | 25 | 29.45 | 0.08 |
| 19 | TBA | 85 | 22 | 2.5 | 29.50 | 0.05 |
| 20 | TBA | 85 | 22 | 25 | 32.18 | 0.08 |

[1]wt-% of the silica content refers to the content of silica in the PDMS elastomer, e.g. sample 1 in table 1 means 90 wt-% xylene with 10 wt-% PDMS elastomer, wherein the elastomer contains 27 wt-% silica.

TABLE 2

| Sample | OD of coated core before assembly (mm) | ID of coated core before assembly (mm) | OD of coated core after assembly (mm) | Core length before assembly (mm) | Core length after assembly (mm) |
|---|---|---|---|---|---|
| 1 | 2.35 | 0.97 | 2.68 | 6.24 | 6.02 |
| 2 | 2.13 | 0.84 | 2.62 | 6.14 | 5.32 |
| 3 | 2.44 | 1.01 | 2.74 | 6.29 | 6.17 |
| 4 | 2.41 | 0.98 | 2.73 | 6.38 | 6.17 |
| 5 | 2.41 | 1.00 | 2.74 | 6.49 | 6.24 |
| 6 | 2.45 | 0.99 | 2.76 | 6.28 | 6.14 |
| 7 | 2.44 | 0.99 | 2.75 | 6.35 | 6.25 |
| 8 | 2.54 | 0.98 | 2.86 | 6.46 | 6.28 |
| 9 | 2.47 | 1.00 | 2.83 | 6.42 | 6.31 |
| 10 | 2.44 | 0.88 | 2.83 | 6.56 | 6.30 |
| 11 | 2.38 | 0.97 | 2.72 | 6.18 | 5.47 |
| 12 | 2.32 | 0.95 | 2.72 | 6.20 | 5.21 |
| 13 | 2.35 | 0.97 | 2.69 | 5.92 | 5.36 |
| 14 | 2.36 | 0.96 | 2.70 | 5.84 | 5.14 |
| 15 | 2.36 | 0.97 | 2.71 | 6.03 | 5.54 |
| 16 | 2.43 | 1.00 | 2.75 | 5.99 | 5.73 |
| 17 | 2.46 | 1.00 | 2.81 | 5.92 | 5.40 |
| 18 | 2.37 | 0.96 | 2.81 | 5.86 | 5.56 |
| 19 | 2.47 | 0.99 | 2.85 | 5.87 | 5.65 |
| 20 | 2.46 | 1.00 | 2.90 | 5.96 | 5.74 |

2.2 IUS Sample Preparation, Continuous Mode

Pieces having a length of 6 mm were cut from the coated tube (core). Weight, length as well as inner and outer diameters of each piece was measured.

Thereafter each piece of coated tube (core) was positioned on a T-frame of an IUS using an assembling tool where pneumatic air is blown through a thin steel pin. The length of each piece as well as the inner and outer diameter of each piece was measured at two different positions after assembly.

Table 3 below illustrates the average values of some samples (samples 21-23), the average having been calculated on the basis of three parallel samples. XYL stands for xylene. Table 3 gives the parameters for the coating solution (solvent, amount of solvent and silica content) as well as the pulling speed used. Weight of the coated poly(dimethyl) siloxanes core as well as the thickness of the coating and the concentration of IND in the core are also given.

TABLE 3

| Sample | Solvent | Amount of solvent (wt-%) | Silica content[2] (wt-%) | pulling speed (mm/s) | Weight of coated core (mg) | Coating thickness (mm) | Conc. IND in core |
|---|---|---|---|---|---|---|---|
| 21 | XYL | 85 | 27 | 6 | 29.7 | 0.06 | 25 wt-% |
| 22 | XYL | 90 | 27 | 15 | 28.6 | 0.03 | 45 wt-% |
| 23 | XYL | 85 | 27 | 13 | 30.8 | 0.09 | |

[2]wt-% of the silica content refers to the content of silica in the PDMS elastomer Table 4 gives the measurement results for the dimensions of the coated tube (core) before assembly on the T-frame, OD standing for outer diameter and ID for inner diameter.

TABLE 4

| Sample | OD of coated core before assembly (mm) | ID of coated core before assembly (mm) | OD of coated core after assembly (mm) | Core length before assembly (mm) | Core length after assembly (mm) |
|---|---|---|---|---|---|
| 21 | 2.4 | 1.02 | — | 6.0 | — |
| 22 | 2.4 | 1.00 | — | 6.3 | — |

3. Drug Release From the IUS Sample

Drug release from IUS samples prepared as described in 2 were studied by placing each IUS sample [i.e. the piece of coated tube (core) and the T-body] in a 150 ml bottle containing 150 ml 1% cyclodextrane solution. Samples of this solution were withdrawn at regular intervals and subjected to ultra-high performance liquid chromatography (UHPLC) using the following parameters (a standard UHPLC, e.g. Agilent 1290 UHPLC, method for Indomethacin analysis).

Eluent: ACN (0.1%)/HCOOH (45:55)
Eluent speed: 0.5 ml/min
Column: UPLC BEH C18 1.7 μm 2.1×50 mm
Temperature of the column: +30° C.
Detection wave length: 244 nm
Sample volume: 10 μl
Duration of run: 3 min The retention time for indomethacin was about 2 minutes.

Figure 2:
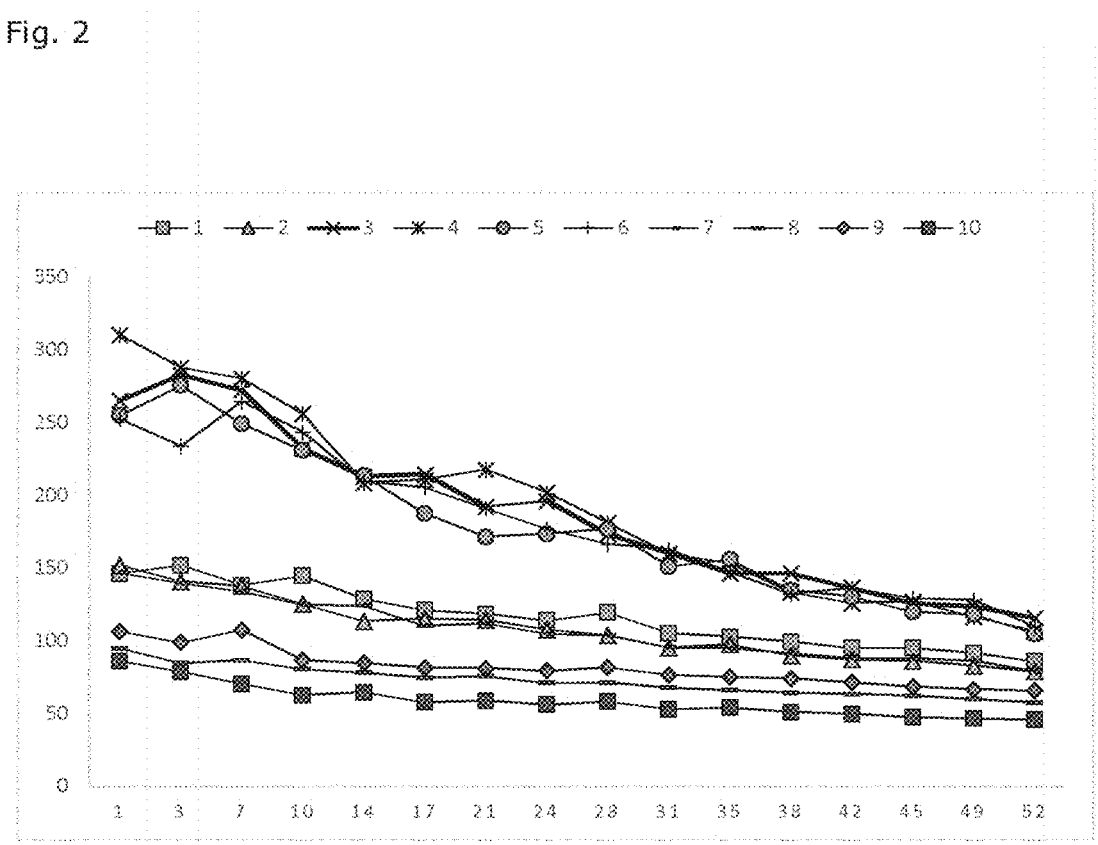
FIGS. 2-5 illustrate some results of the drug release experiments.
Figure 3:
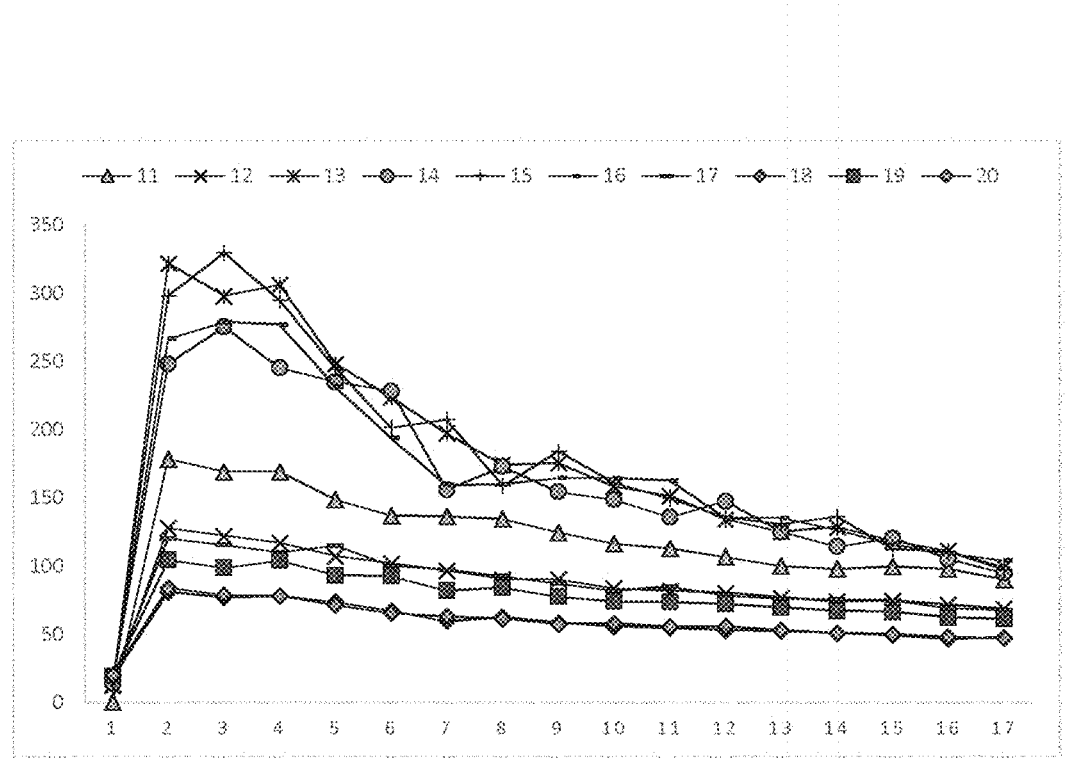
Figure 4:
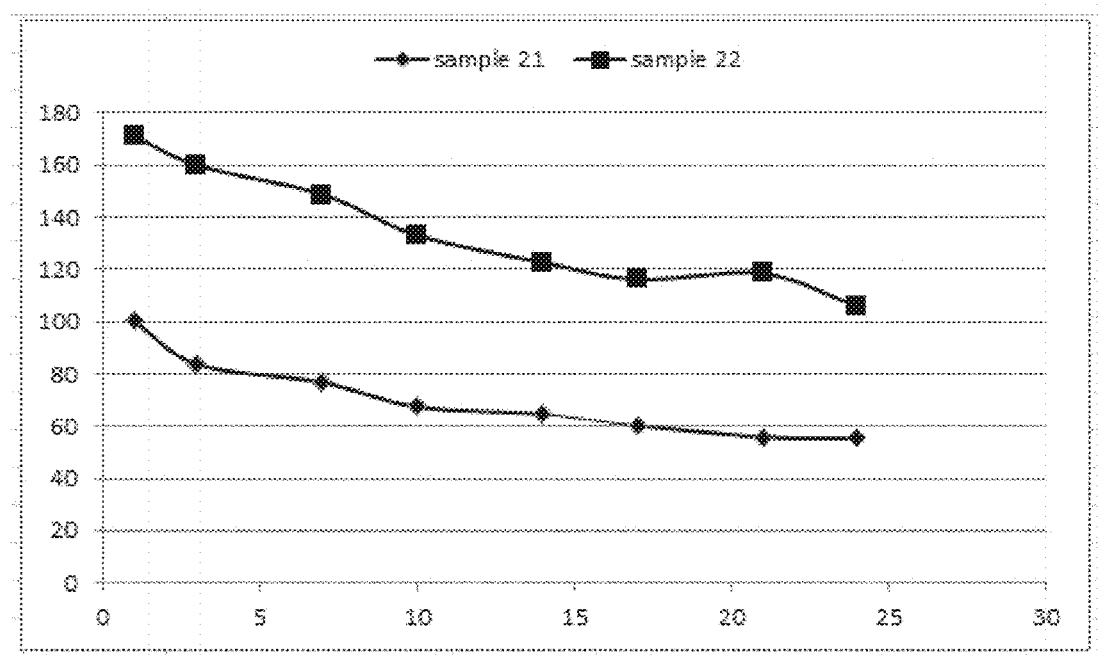

The results for samples 1-10 are illustrated in FIG. 2, while those for samples 11-20 are shown in FIG. 3. The release of samples 21-22 is shown in FIG. 4. The results are expressed as micrograms/day (abscissa) for different durations of the test expressed in days (ordinate).

Figure 5:
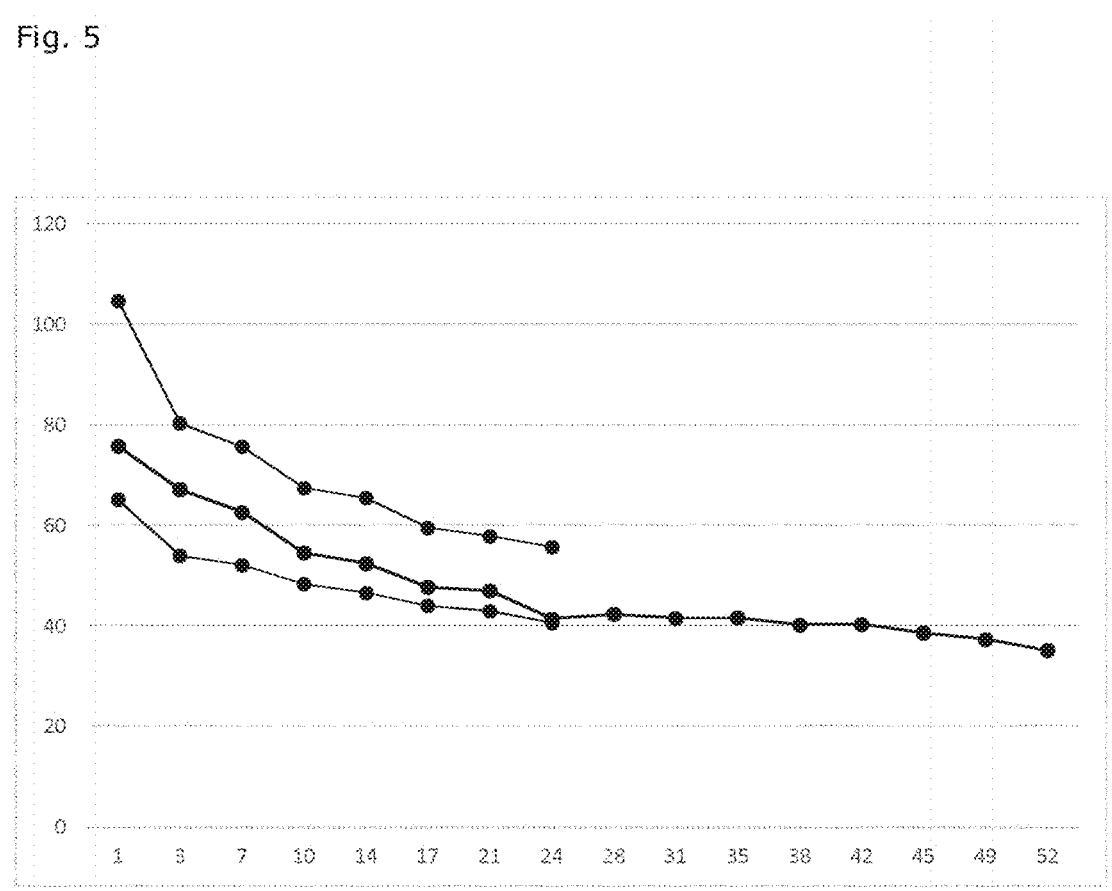

The results for groups A, B and C are shown in FIG. 5, expressed as micrograms/day (abscissa) for different durations of the test (in days, ordinate). The uppermost curve corresponds to group B, the middle curve (longest) corresponds to group A. The lowest curve corresponds to group C. The number of parallel samples tested was 10 for group A and six for each of groups B and C. The results in FIG. 5 are the average values for drug release for the total of parallel samples tested. The duration of the test was 52 days for group A and 24 days for each of groups B and C.

The total amount of impurities in the released drug (i.e. degradation products of indomethacin) was also measured and it was 0.12 wt-% for group A, 0.09 wt-% for group B and 0.10 wt-% for group C. Double or triple curing did thus not result in increase of impurities in the drug, despite the increased heat load on the samples.

The invention claimed is:

1. A method for modifying release of a therapeutically active agent from an elastomeric matrix, comprising:
    providing a core comprising indomethacin and an elastomeric matrix of poly(dimethyl) siloxane (PDMS);
    dipping the core into a coating solution comprising 15% PDMS elastomer comprising 27 wt. % of silica, calculated from the total amount of silica and elastomer, and a solvent comprising xylene; and
    curing the dipped core to provide a coated core,
    wherein dipping the core is a continuous process comprising pulling the core through the coating solution using a pulling speed from 6-15 mm/s and suitable for providing a coating thickness of 5-90 μm.

2. The method of claim 1, wherein the elastomer of the coating solution contains cross-linking agents or catalyst as additives.

3. The method of claim 1, wherein the amount of solvent in the coating solution is 60-95 wt %.

4. The method of claim 1, wherein the curing is carried out using at least one of infrared radiation, ultraviolet radiation and heat.

5. The method of claim 1, wherein the core comprises 25 wt-% indomethacin calculated from the total amount of indomethacin and elastomer matrix.

6. The method of claim 1, wherein the core comprises 45 wt-% indomethacin calculated from the total amount of indomethacin and elastomer matrix.

7. The method of claim 1, wherein the thickness of the coating is from 30 to 90 μm.

8. The method of claim 1, wherein a curing time is done in batch mode and wherein the curing time is 10-60 seconds.

9. The method of claim 1, wherein a curing time is done in continuous mode and wherein the curing time is 100-150 seconds.

10. A method for modifying release of a therapeutically active agent from an elastomeric matrix, comprising
    providing a core comprising indomethacin and an elastomeric matrix comprising poly(dimethyl) siloxane;
    dipping the core to a coating solution comprising 5-25 wt % of an elastomer containing 20-35 wt-% of a filler, calculated from the total amount of filler and elastomer, and a solvent comprising xylene; and
    curing the dipped core to provide a coated core,
    wherein the dipping is provided as a continuous process by pulling the core through the coating solution using a pulling speed of 5-25 mm/s, the filler is selected from silica, titanium dioxide, barium sulphate, carbon and mixtures thereof, and the elastomer of the coating solution comprises one or more of poly(dimethyl) siloxanes, polyethylene vinyl acetates (EVAs), polyurethanes (PUs), polyhydroxyethyl methacrylates (PHEMAs) and polymethyl methacrylates (PMMAs).

* * * * *